United States Patent [19]
Collins et al.

[11] Patent Number: 5,455,590
[45] Date of Patent: Oct. 3, 1995

[54] REAL-TIME HOLOGRAPHIC SURVEILLANCE SYSTEM

[75] Inventors: H. Dale Collins; Douglas L. McMakin, both of Richland; Thomas E. Hall, Kennewick; R. Parks Gribble, Richland, all of Wash.

[73] Assignee: Battelle Memorial Institute, Richland, Wash.

[21] Appl. No.: 212,432

[22] Filed: Mar. 14, 1994

Related U.S. Application Data

[63] Continuation-in-part of Ser. No. 963,204, Nov. 23, 1992, abandoned, which is a continuation-in-part of Ser. No. 752,750, Aug. 30, 1991, abandoned.

[51] Int. Cl.$^6$ .............................. G01S 13/89; G03H 5/00
[52] U.S. Cl. .................................. 342/179; 367/8
[58] Field of Search .................... 342/179; 367/8

[56] References Cited

U.S. PATENT DOCUMENTS

| | | | |
|---|---|---|---|
| 5,073,782 | 12/1991 | Hugenin et al. | 342/179 |
| 5,142,255 | 8/1992 | Chang et al. | 343/767 |
| 5,170,170 | 12/1992 | Soumekh | 342/179 |

FOREIGN PATENT DOCUMENTS 2034554  6/1980  United Kingdom.

OTHER PUBLICATIONS

Ynguesson et al, "Endfire Tapered Slot Antennas on Dielectric Substrates" IEEE Trans on Antennas and Propagation, vol. Ap. 33, No. 12, Dec. 1985.

A. L. Boyer, et al., Reconstruction of Ultrasonic Images by Backward Propagation, Ch. 18, 7/70, pp. 333–349.

H. D. Collins, Error Analysis in Scanned Holography, 1970, Thesis, Oregon State University.

B. P. Hildebrand, et al, An Introduction to Acoustical Holography, 1974, pp. vii, 20–21.

Aoki et al, Diagnosis of Under–Snow Radar Images by Three Dimensional Displaying Technique in Holographic Imaging Radar, Proc. of IGARSS '87 Symposium, May 18–21, 1987, pp. 571–576.

*Primary Examiner*—Ian J. Lobo
*Attorney, Agent, or Firm*—Paul W. Zimmerman

[57] ABSTRACT

A holographic surveillance system including means for generating electromagnetic waves; means for transmitting the electromagnetic waves toward a target at a plurality of predetermined positions in space; means for receiving and converting electromagnetic waves reflected from the target to electrical signals at a plurality of predetermined positions in space; means for processing the electrical signals to obtain signals corresponding to a holographic reconstruction of the target; and means for displaying the processed information to determine nature of the target.

The means for processing the electrical signals includes means for converting analog signals to digital signals followed by a computer means to apply a backward wave algorithm.

18 Claims, 10 Drawing Sheets

$T_0$ to $T_1$ = 1.5 $\mu$sec

REAL-TIME HOLOGRAPHIC SURVEILLANCE SYSTEM

STATEMENT OF GOVERNMENT INTEREST

This invention was made with Government support under Contract DE-AC06-76RLO 1830, awarded by the U.S. Department of Energy. The Government has certain rights in the invention.

This application is a Continuation-In-Part of U.S. patent application Ser. No. 07/963,204, filed Nov. 23, 1992, now abandoned, which is a Continuation-In-Part of U.S. patent application Ser. No. 07/752,750, filed Aug. 30, 1991, now abandoned.

FIELD OF THE INVENTION

The present invention relates to a method and apparatus useful for inspection of concealed objects. More specifically, the present invention relates to use of backward wave propagation analysis with millimeter wave signals that are transmitted and received by a holographic array. The method and apparatus have particular utility for personnel inspection in mass transportation centers.

BACKGROUND AND RELATED ART

The need for a new and more versatile personnel inspection system in mass transportation centers has increased in recent years. Traditional inspection systems such as metal detectors and x-ray imaging systems, although capable of near real-time detection, have limitations and adverse effects in the detection of concealed targets. Limitations of metal detectors include the inabilities to (a) provide precise target location, (b) detect plastic concealed weapons, and (c) detect certain metals because of sensitivity variation for various metals. Limitations of X-ray imaging of personnel include radiological health effects. Consequently, holography has been under investigation as an alternative or complementary approach to personnel inspection.

Related holographic art known to the inventors includes the following. A report, EVALUATION OF PASSIVE FAR INFRARED RADIOMETRIC TECHNIQUES FOR DETECTION OF CONCEALED OBJECTS, DT Hodges et al., Aerospace Report No. ATR-79(7745)-1, Contract No. At-(29-1)789, Sandia Laboratories, Albuquerque, NM, 87115, Mar. 1979, p. 41, discloses apparatus and a process for far infrared detection of concealed objects. U.S. Pat. No. 4,841,489 to Ozaki et al. discloses a method for imaging an object or substance by ultrasonic or electromagnetic waves based on a synthetic aperture method capable of economizing memory capacity, achieving real-time base image reproduction, and obtaining a high quality image.

Application of holography to the problem of personnel surveillance has been limited because of the inability to either (a) produce an image of sufficient resolution, or (b) produce an image in near real-time, or (c) a combination of both. It is recognized that use of millimeter wave electromagnetic radiation is not a physiological health hazard and such radiation penetrates certain materials, including but not limited to clothing.

Prior work as reported by NH Farhat, HIGH RESOLUTION MICROWAVE HOLOGRAPHY AND THE IMAGING OF REMOTE MOVING OBJECTS, Optical Engineering, Sep. -Oct. 1975, Vol. 15, No. 5, pp. 499–505, utilized millimeter wave holography in working toward surveillance systems. However, Farhat did not obtain high resolution because he used f-numbers greater than 1.0. Moreover, he could not achieve near real-time imaging because he used an optical reconstruction technique.

Hildebrand and Brendan, AN INTRODUCTION TO ACOUSTICAL HOLOGRAPHY, 1972, Plenum Press, New York, NY, demonstrated excellent resolution with acoustical holography using optical reconstruction and a low f-number. However, it is recognized that acoustical holography is impractical for personnel surveillance because of the coupling fluid required between the acoustic transmit/receive element and the target. Moreover, Hildebrand and Brendan used optical reconstruction that cannot achieve near real-time imaging.

Both Farhat and Hildebrand et al. used optical reconstruction to produce images with their holograms. Another reconstruction technique is digital reconstruction wherein the signal reflected from the target in the form of acoustic or electromagnetic radiation is converted into a digital electronic signal that is mathematically converted into information that is useful for producing an image of the target. Even using digital reconstruction techniques, however, high resolution is not always obtainable because the reconstruction techniques inherently limit image resolution.

There are standard digital reconstruction techniques that have been used for processing millimeter wave data. For example, a widely used method is to apply a fast Fourier transform to the Kirchoff diffraction integral. However, this method uses a finite sum written in the small angle (Fresnel) approximation that limits the relationship between aperture size and distance to the target, inherently limiting the f-number to be at least 6, and thereby limiting resolution of holographic image reconstruction.

A digital reconstruction method that overcomes this limitation is reported by AL Boyer et al., RECONSTRUCTION OF ULTRASONIC IMAGES BY BACKWARD PROPAGATION, Reconstruction of Holographic Images, Chapter 18, July 1970. The so-called angular spectrum backward wave propagation method does not use the Fresnel approximation and can therefore be used for low f-number reconstruction. However, the angular spectrum method has not been widely used for holographic imaging because it is generally believed that the recording plane must be very stable and flat within a small fraction of the wavelength. A thesis by H. D. Collins, Jun. 1970, demonstrates that the recording plane need not be flat within a wavelength. Another reason that the angular spectrum method has not been widely used is that it is computationally intensive, requiring up to 30 minutes for data reduction and reconstruction on an IBM 360/Mod 44 for the first plane, and 5 minutes each for subsequent planes.

The second fundamental limitation preventing wide use of millimeter wave holography for personnel surveillance is the amount of time required to scan a target. Boyer et al. acoustic target scanning required 50 minutes to obtain 300 samples/second in 256 scan lines. Boyer et al. restricted scan rates to obtain highest spatial frequency. Use of a single antenna element moved from position to position for 65,000 positions across an aperture has been accomplished in 5 minutes. To be useful in surveillance, it is necessary to perform a scan within several seconds and preferably in one second or less.

In holography, fast scans with high resolution are difficult to achieve. Resolution is highest when the millimeter wave signal is transmitted and received from the same antenna element. As previously indicated, moving a single element to hundreds of positions is physically limited to scan times on the order of minutes. Use of separate transmit and receive arrays severely limits the resolution of the reconstructed image. Examples of scanning systems include various arrangements of antenna types and arrays.

Antenna arrays have been used as reported in Tricoles et al., MICROWAVE HOLOGRAPHY: APPLICATIONS AND TECHNIQUES, Proceedings of the IEEE, Vol. 65, No. 1, January 1977. In FIGS. 4 and 5 of Tricoles et al., arrays are shown wherein antenna element spacing is much greater than a wavelength of the microwaves and there are separate transmit and receive arrays.

Larson et al., MICROWAVE HOLOGRAM RADAR IMAGERY, February 1972, show a far-field microwave holographic imaging system having a single transmit horn antenna and a separate receiver array of 100 elements spaced slightly more than ½ wavelength apart. FIG. 11 of Larson et al. shows an image of a Jeep made with this system. The image resolution is coarse, 15 cm (½ foot) by 15 cm (½ foot).

Thus, there is a need for a holographic image reconstruction method and apparatus that can provide high resolution with fast scanning and fast reconstruction algorithm to accomplish near real-time imaging that is needed for personnel surveillance.

BRIEF DESCRIPTION OF THE INVENTION

The invention disclosed herein involves a method and apparatus for achieving near real-time holographic imaging of concealed objects. Millimeter wave radiation above about 26.5 GHz can penetrate materials such as clothing and provide high resolution images on the order of about 1.13 cm at 26.5 GHz, and about 0.27 cm at 110 GHz. With high resolution images, target identification and location are possible.

High resolution is preserved in the image reconstruction by using the angular spectrum backward wave propagation analysis instead of the Kirchoff analysis, thereby permitting exact image reconstruction for f-numbers of 1 or less.

Near real-time imaging is achieved by (1) performing the angular spectrum backward wave propagation on state-of-the-art computers, and (2) by providing a holographic array and switching bank capable of fast scanning.

The present invention may be applied to provide high resolution target identification and location on a suspect and/or an electronic frisk of a suspect with or without the suspect's knowledge. The present invention may be used alone or in combination with other surveillance equipment to provide additional surveillance capability in near real-time at personnel check points. The present invention permits application of a detection system that is not sensitive to different metal types and can detect non-metal weapons such as those made of plastic.

A general embodiment of the invention provides for a holographic surveillance apparatus wherein the target is in close proximity to the surveillance apparatus. Close is defined as from about 10 cm (5 inches) to about 100 cm (50 inches). The apparatus includes a holographic array means for simultaneously transmitting and receiving electromagnetic waves toward and from a target from successive antenna units in the array; means for providing a cone angle of the electromagnetic waves resulting in an f-number of from about 0.1 to about 10; means for processing the received electromagnetic waves to obtain amplitude and phase information for constructing a holographic image; and means for displaying the holographic image. Although the received electromagnetic waves may be reconstructed optically or digitally, it is preferred to use digital reconstruction. An optional video means for optically monitoring the target may be used.

DETAILED DESCRIPTION OF THE INVENTION

The following description begins with a description of a holographic transceiver system followed by a section on millimeter wave holography theory using the angular spectrum backward wave propagation method. Operational Examples are then given, followed by further detail of construction of a millimeter wave holographic imaging system.

HOLOGRAPHIC TRANSCEIVER SYSTEM

Figure 1:
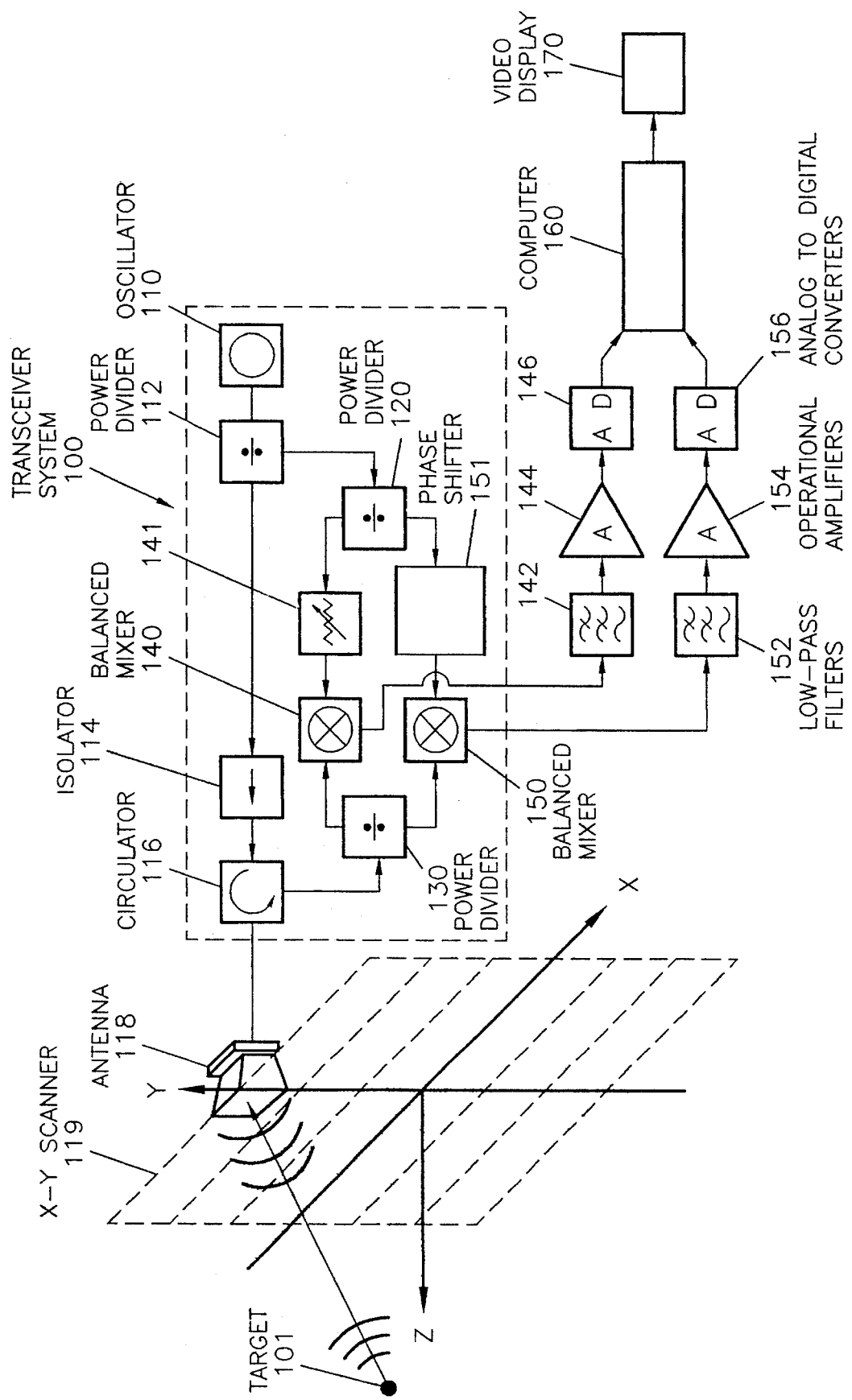
FIG. 1 is a semi-schematic diagram of one embodiment of the invention depicting a simplified scanned, one element, millimeter wave holographic system.

As an example, consider the simplified scanned—one element—millimeter wave holographic transceiver system 100 shown in FIG. 1. The oscillator 110 provides a source of millimeter wave energy for both detecting the target 101 and for providing reference signals. In this example the oscillator 110 is a continuous wave, coherent source. Signals from the oscillator 110 are divided by the first power divider 112 so that part of the signal is sent to the second power divider 120 for use as a reference signal in the balanced mixers 140, 150, with the remainder of the signal transmitted to the isolator 114. The isolator 114 is a rectifying device that is able to transmit millimeter waves in one direction (arrow), but not in the other. The isolator 114 prevents millimeter waves reflected from the target 101 from returning to the oscillator 110, which would impair its operation. The circulator 116 directs the millimeter waves reflected from the target 101 to the third power divider 130, and directs millimeter wave energy from the oscillator 110 to be transmitted to the single horn transceiver antenna 118 but not to the third power divider 130. Millimeter waves from the holographic transceiver 100 are radiated by the antenna 118. The antenna 118 transmits the millimeter waves to the target and also receives the target's reflected waves. The phase and amplitude data from the received waves is then sent to the holographic processor (computer) 160 as described below.

Note that the illustration embodied in FIG. 1 is only a single element system where the antenna 118 is scanned in an X-Y scanner 119 to fill the aperture. The electronic scan is made up of transmitting and receiving a signal from an individual antenna unit in sequence one at a time in successive order. Electronic millimeter wave switches are used to direct signals to the antenna units. An antenna unit may be a single antenna (monostatic) that both transmits the source signal and receives the reflection signal from the target. Alternatively, the antenna unit may be two antennas (bistatic) in which one antenna transmits the source signal and the other antenna receives the reflection signal from the target.

In a multi-antenna unit linear array system, the linear array may be mechanically scanned in one direction (e.g., vertical) and electronically scanned in the other (e.g., horizontal). Alternatively, in a multi-antenna unit planar array system, the array would be electronically scanned in both directions.

Thus, the target 101 is illuminated by a source of radiation from the antenna 118. The point reflector 101 reflects millimeter waves that emanated from the antenna 118 back to the same antenna 118.

THEORY OF OPERATION USING ANGULAR SPECTRUM BACKWARD WAVE PROPAGATION

In FIG. 1, the plane 102 may be defined as $(x,y,z=0)$, and a point 101 on a target may be defined as $(x_o,y_o,z_o)$, thereby permitting the reflected signal to be written as $$E_o(x_i)=A(x_o,y_o,z_o) \cos [\omega t+\phi_o(x,y)] \quad (1)$$

where $\omega$=radian frequency $r$ = distance from the antenna to the object point, written as $$r = \sqrt{(x-x_o)^2 + (y-y_o)^2 + z_o^2}$$

$$\phi_o(x,y) = \frac{2\pi}{\lambda} r(x,y) = \text{phase of target}$$

and A=reflected amplitude of the target point.

The received signal is sent to a circulator 116 that allows the signal from waves reflected from the target to be sent to the third power divider 130, but not toward the millimeter wave oscillator 110. When the signal reaches the power divider 130, it is equally split into two channels. One channel is called the in-phase "I" leg 140+, and the other is the quadrature "Q" leg 150+. Thus, the signal enters balanced mixers 140,150, which detect the phase and amplitude of the signal. The balanced mixer 140 is referenced to the oscillator signal from the second power divider 120, in phase, by the signal attenuator 141. The other balanced mixer 150 is referenced to the oscillator signal from the second power divider 120, in quadrature (90°), by phase shifter 151. The signal attenuator 141 is used to adjust the amplitude of the signal in the in-phase leg at the balanced mixer 140. This power adjustment capability is necessary because the power of the balanced mixer in the quadrature leg is decreased due to the phase shifter 151. In addition, for optimum operation, the local oscillator signal power must be the same at the balanced mixers 140,150.

Signals from the balanced mixers 140,150 are then further processed by low-pass filters 142,152. The output from the balanced mixers 140,150 is the sum and difference of the frequency of the local oscillator 110 and the signal reflected from the target 101. Additionally, phase information of the reflected signal referenced to the oscillator is also sent on to the computer 160. Since the frequency of the oscillator and reflected target signal are the same, the sum of the two frequencies is two times the oscillator frequency, and the difference is zero. However, phase information is in both the sum and the difference frequencies. It is easier electronically to extract the amplitude and phase information from the difference frequency than the sum frequency, because the sum frequency is a very high frequency. The low pass filters 142,152 thus pass the difference frequency with its phase information on to operational amplifiers 144,154. Operational amplifiers 144,154 are used to increase the gain of the in-phase "I" and quadrature "Q" signals. The gains of the operational amplifiers 144,154 are set to match the maximum range of the analog to digital (A/D) converters 146, 156. The A/D converters 146,156 change the analog in-phase and quadrature signals from the operational amplifiers 144,154 to 12-bit digital signals. Digital information from the in-phase and quadrature signals from the A/D converters 146,156 is processed by a digital-holographic-reconstruction system as computer 160 that converts the information to a form allowing visual display of the holographic image on video display 170.

Proceeding with the mathematical computation after low pass filtering, the result is two parts of a hologram, a real part $S_R(x,y)$ and an imaginary part $S_I(x,y)$ of the complex signal. That is, $$S_R(x,y)=A(x_o,y_o,z_o) \cos \phi_o(x,y)$$

$$S_I(x,y)=A(x_o,y_o,z_o) \sin \phi_o(x,y) \quad (2)$$

Thus, both amplitude of the reflected signal and distance to the target point have been preserved. They can be independently extracted by the operations $$A(x_o, y_o, z_o) = |S_R(x,y) + iS_I(x,y)| \quad (3)$$

$$r(x,y) = \frac{1}{\beta} \tan^{-1}\left(\frac{S_I}{S_R}\right) = \frac{\phi_o(x,y)}{\beta}$$

where $$\phi = \text{phase and } \beta = \frac{2\pi}{\lambda}$$

By superposition, one can argue that the target can be made up of a large number of points, and that the signal at (x,y) is a summation of individual reflections. Thus, if the x-y plane 102 is fully scanned, and $S_R, S_I$ is measured and recorded, everything about the reflectivity of the target is preserved.

To illustrate the use of the angular spectrum backward wave propagation method for image reconstruction, a further example considers the case where Equation (2) is written in more general terms. An antenna is scanned in some plane (x,y) 102 where z=constant, and the wave-front reflected from a target is recorded. The equation is written as $$f(x,y,z) = g(x,y,z) \exp[j\phi_o(x,y,z)] \quad (4)$$

where g=amplitude and $\phi_o$=phase of the wave as a function of position.

Since the radiation obeys the rules of wave theory, it is necessary that the recorded wave be propagated according to the same rules in order to retrieve the wavefront in its original position in space.

Equation 4 is then subjected to the angular spectrum backward wave propagation method to simply decompose the recorded wavefront into individual plane waves propagating in different angular directions as suggested by Boyer et al. The process of propagation induces a phase change on each plane wave as it propagates from one plane to the next. The composite wave can then be reconstructed by vector summation of the plane wave components.

Using the plane wave components in digital form, the two-dimensional Fourier transform of f(x,y,z) is computed, $$F(u,v,z) = \iint f(x,y,z) \exp[-2\pi j(ux+vy)] dx dy \quad (5)$$

and conversely, $$f(x,y,z) = \iint F(u,v,z) \exp[2\pi j(ux+vy)] du dv \quad (6)$$

In propagating from the z plane to a z' plane, f must obey Helmholtz's equation $$\nabla^2 f + \left(\frac{2\pi}{\lambda}\right)^2 f = 0 \quad (7)$$

Inserting Equation (6) into Equation (7), one obtains $$\iint \left\{ \frac{\partial^2 F}{\partial(z'-z)^2} + \left[\left(\frac{2\pi}{\lambda}\right)^2 - (2\pi u)^2 - (2\pi v)^2\right] F \right\} \cdot \quad (8)$$

$$\{\exp[2\pi j(ux+vy)]\} du dv$$

This relation holds for all x,y if $$\frac{\partial^2 F}{\partial(z'-z)^2} + \left(\frac{2\pi}{\lambda}\right)^2 [1-(\lambda u)^2-(\lambda v)^2] F = 0 \quad (9)$$

The solution to equation 8 has two parts, F+ and F−

$$F(u,v,z') = \quad (10)$$

$$F^+(u,v)\exp\left\{\frac{-2\pi j}{\lambda}[1-(\lambda u)^2-(\lambda v)^2]^{1/2}(z'-z)\right\} +$$

$$F^-(u,v)\exp\left\{\frac{2\pi j}{\lambda}[1-(\lambda u)^2-(\lambda v)^2]^{1/2}(z'-z)\right\}$$

where $F^+$ represents the Fourier transform (angular spectrum) of the wave propagating toward the far field. Waves propagating toward the far field are not focused, and the exponential term represents a forward wave propagator.

The second part of the solution of Equation 8, $F^-$ represents the Fourier transform (angular spectrum) of the wave propagating from the received plane (z=0) back towards the target. Waves propagating toward the near field are focused, and so it is this second part of the solution that is relied upon for imaging, and the exponential term represents a backward wave propagator.

A near-field image is one in which the image is made using waves that are near enough to a source to still have a substantial curvature as opposed to a far-field image made from waves having substantially no curvature, or plane waves. The near-field is generally considered to be two times the ratio of the square of the target diameter to the wavelength.

For radiation in the backward direction (i.e., towards the target), one utilizes $F^-$ by setting $F^+$=0. Then using initial conditions, one finds $F^-(u,v) = F^-(u,v,z)$ and $$F^-(u,v,z') = \quad (11)$$

$$F^-(u,v,z)\exp\left\{\frac{2\pi j}{\lambda}[1-(\lambda u)^2-(\lambda v)^2]^{1/2}(z'-z)\right\}$$

which is a product of the Fourier transform and the backward wave propagator giving a plane wave angular spectrum at the target plane.

Taking the inverse Fourier transform of Equation 12, one obtains the target image $$f(x,y,z') = \quad (12)$$

$$\iint F(u,v,z)\exp\left\{\frac{2\pi j}{\lambda}[1-(\lambda u)^2-(\lambda v)^2]^{1/2}(z'-z)\right\} \cdot$$

$$\exp\{2\pi j(ux+vy)\} du dv$$

The target image f(x,y,z') is squared to obtain an intensity image that is used for plotting the results and forming a visual image.

Thus, in summary, from the target's scattering wave field (i.e., near-field) (Equation 5) in one plane, one can calculate the field at the target from four sets of instructions:

(1) A first set of instructions for computing a two-dimensional Fourier transform of the given field f(x,y,z) (Equation 5) from the phase and amplitude information (real and imaginary holograms of Equation 2) obtained from the high frequency millimeter wave radiation reflected from the target;

(2) A second set of instructions for multiplying the Fourier transform by the complex backward wave propagator $$\exp\left\{\frac{2\pi j}{\lambda}[1-(\lambda u)^2-(\lambda v)^2]^{1/2}(z'-z)\right\}$$

where z'−z is the distance from the antenna array to the target. The multiplication forms a plane wave angular spectrum at the target plane. If desired, different focus planes z* may be calculated, to obtain the optimum viewing image, by changing the z' value to vary the distance to the target;

(3) A third set of instructions for computing an inverse transform of the plane wave angular spectrum at the target plane yielding f(x,y,z'), a target image (Equation 12); and (4) A fourth set of instructions for computing a target intensity image $|f(x,y,z')|^2$ from the target image. The target intensity image is used for plotting the results (e.g., viewing screen).

The algorithm operations described above are performed on the received signals by the computer and converted for video display. The resultant high resolution image uniquely identifies the scattering points on the target and readily identifies the target.

Carrying out the computations on a computer system permits holographic image reconstruction within 1 second.

EXAMPLE 1

Figure 2:
FIG. 2A shows an optical picture of a mannequin with a metal gun beneath a cotton/acetate suit jacket.
FIG. 2B shows the mannequin imaged with a simulated holographic linear array at 35 GHz.
Figure 2:
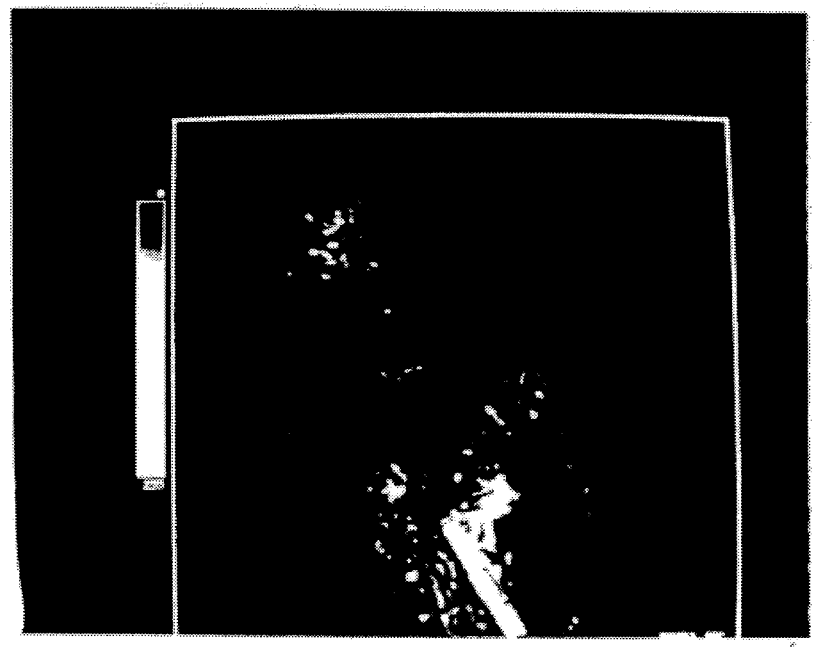
Figure 3:
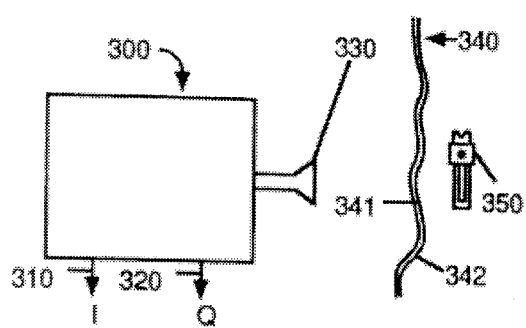
FIG. 3A illustrates the 35 GHz imaging setup used for FIGS. 3C and 3D.
FIG. 3B is an optical picture of a handgun with a plastic handle (model Glock 17).
FIG. 3C is a holographic image at 35 GHz of the same handgun in air with no other intervening barrier material.
FIG. 3D is a holographic image at 35 GHz of the same handgun imaged through two layers of clothing at 35 GHz.
Figure 3:
Figure 3:
Figure 3:
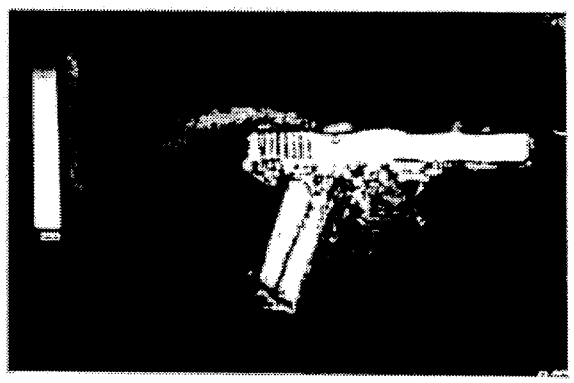

FIG. 2a shows an optical picture of a mannequin with a pellet gun, completely of metal, beneath a cotton/acetate suit jacket that was used as the target subject. FIG. 2b shows the mannequin imaged with a simulated holographic linear array at 35 GHz. The cotton/acetate jacket is easily penetrated by the millimeter waves and the metal pellet gun is readily detected. A holographic linear array (as well as a planar array) was simulated mechanically by physically moving the single antenna 118 of FIG. 1 with an X-Y scanner 119 in the x-y plane, to different positions about one-fourth wavelength apart, until an acceptable image as shown in FIGS. 3C–D was obtained. The results were summed and stored in the computer 160 as if an antenna 118 were located at each position. The number of positions in the x direction was 256 and the number in the y direction was 256, or a total of 65,536 positions of the antenna. This scan required approximately 5 minutes and reveals the time limitations of using a single element antenna where both the x and y axis must be mechanically scanned. Thus, linear antenna arrays or planar antenna arrays as further discussed herein are preferred. The clarity of the reconstructed image (FIG. 2b) demonstrates high resolution achievable with simultaneous transmit/receive antenna element(s), together with f-number of 1 or less and digital reconstruction using the angular spectrum backward wave propagation method.

EXAMPLE 2

FIG. 3a illustrates the test setup used for FIGS. 3c and 3d. The 35 GHz holographic transceiver system 300 is similar to the one discussed in FIG. 1. The leads 310,320 carry the in-phase and quadrature signal information, respectively, to the computer 160. The horn antenna 330 (in a monostatic system as in FIG. 1, using an X-Y scanner 119) was used to transmit and receive the 35 GHz signal. An image was obtained as in Example 1. However, instead of using a mannequin, an optically opaque barrier of clothing 340 placed 18 cm from the antenna 330, comprised of a first layer of 100 percent heavy wool 341 and a second layer of 100 percent light polyester 342, was used to hide a Glock (model 17) handgun 350 having a plastic handle. FIG. 3b is an optical picture of the handgun 350. FIG. 3c is a holographic image of the handgun 350 in air without the clothing 340. FIG. 3d shows the handgun 350 imaged through the two layers of clothing at 35 GHz. A comparison between the handgun 350 imaged in air and behind the clothing reveals that little or no degradation occurs due to the clothing 340 and demonstrates the ability of millimeter wave holography to image a target of multiple materials.

EXAMPLE 3

Figure 4:
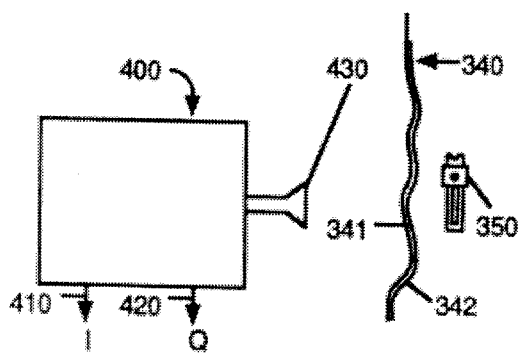
FIG. 4A illustrates the 90 GHz imaging setup used for FIGS. 4C and 4D.
FIG. 4B is an optical picture of the same handgun as in FIG. 3B.
FIGS. 4C–D are holographic images of the same handgun as in FIGS. 3C–D, imaged through the same two barrier materials, but with a 90 GHz holographic system.
Figure 4:
Figure 4:
Figure 4:
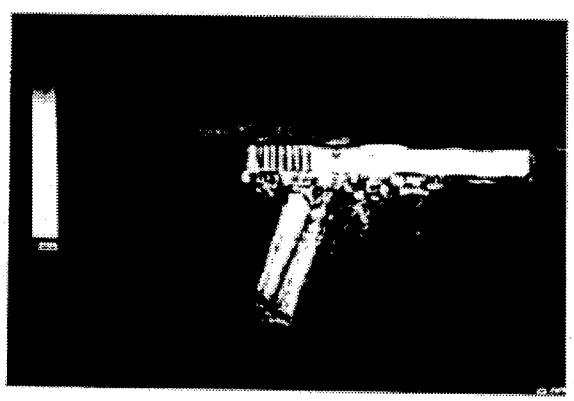

FIG. 4a illustrates the test setup used for FIGS. 4c and 4d. The 90 GHz holographic transceiver system 330 is similar to the one discussed in FIG. 1. The leads 410,420 carry the in-phase and quadrature signal information, respectively, to the digital holographic reconstruction system and visual display. Horn antenna 430 in a monostatic system was used to transmit and receive the 90 GHz signal. An image was obtained as in the method of Example 2. Distance between the horn antenna 430 and the clothing 340 was 18 cm. FIG. 4b is an optical picture of the handgun 350. FIG. 4c is a holographic image of the handgun 350 in air. FIG. 4d shows the handgun 350 imaged through the same two layers of clothing 34 as in FIG. 3d. Again, little degradation occurs due to the barrier materials; however, the holographic images at 90 GHz show much better resolution than the 35 GHz system.

ADDITIONAL FEATURES

Figure 5:
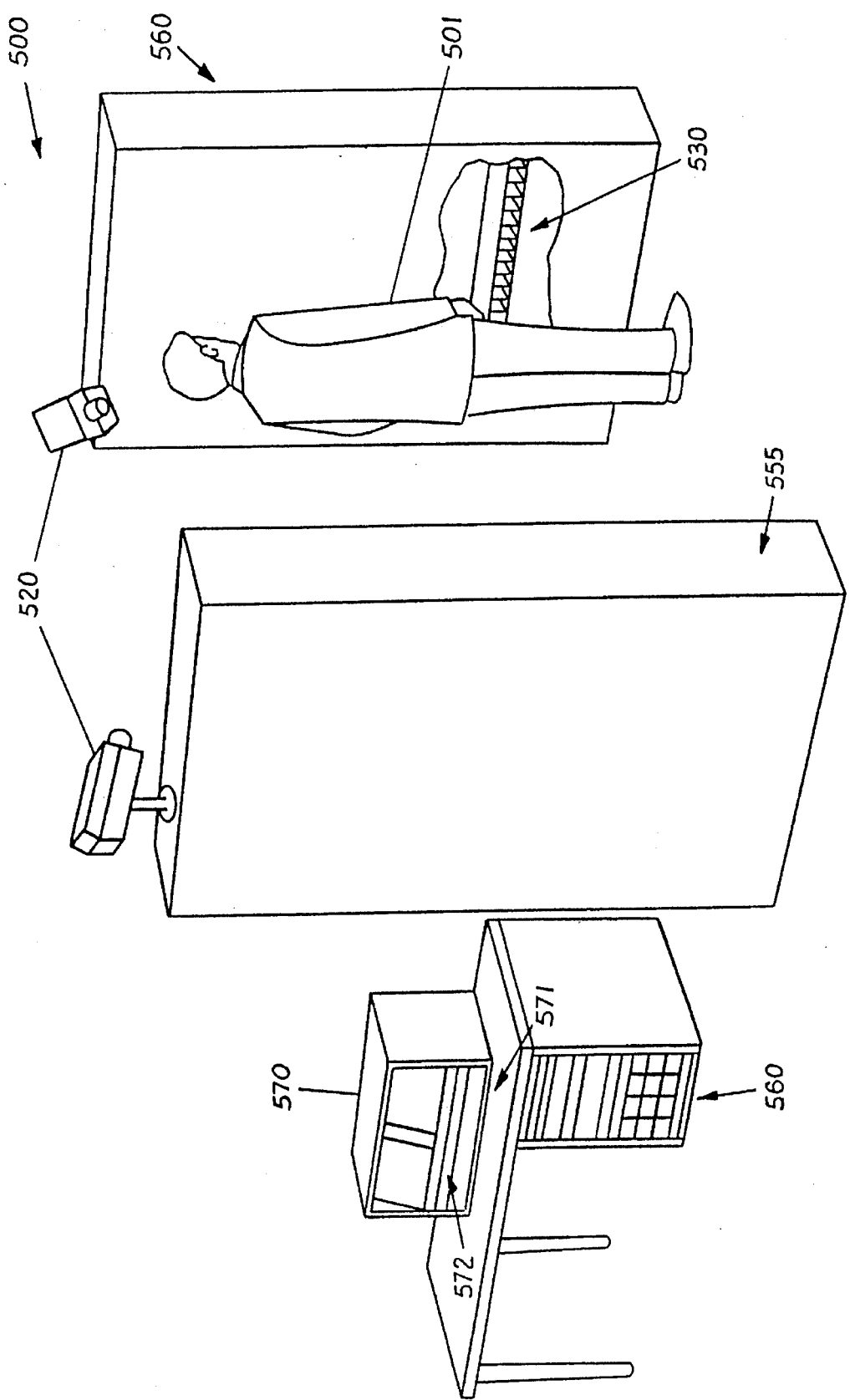
FIG. 5 shows one embodiment for the millimeter wave holographic surveillance system.

FIG. 5 shows an integrated, linear millimeter-wave, holographic surveillance system 500. FIG. 5 shows the main system components for detecting weapons or other items under clothing barriers or in carry-on items such as luggage. In the operation of one embodiment of the invention, an individual 501 is optionally monitored by one or more video cameras 520. The video camera 520 may be of the typical surveillance type. The purpose of the optional video camera 520 is to identify and/or record an individual's optical image and match it with the holographic image. This is helpful since the millimeter wave radiation at the frequencies between about 1 to about 110 GHz does not reflect well enough from low dielectric materials like skin to image the details of the human face. At the same time, the individual is monitored with millimeter waves emanating from a transceiver 530 within a scanner 550. The transceiver 530 is shown having a horizontal linear antenna array, and the scanner 550 would move the transceiver 530 vertically to complete a scan. The transceiver 530 is thus scanned mechanically in a vertical direction and scanned electronically horizontally.

Signals from the transceiver 530 are sent to computer means such as the computer system 560. The computer system 560 performs the holographic algorithm discussed above and the digital holographic reconstruction. Finally, the video display 570 shows a visual image 571 and a holographic image 572 of the individual along with any concealed items such as weapons.

Materials through which the apparatus is able to scan and provide detection of concealed objects includes the low-loss tangent dielectric materials such as clothing, plastics, natural and processed plant materials (such as woven materials, wood, leather, and the like), glass, epoxies, Kevlar, and the like. With the preferred system of the invention, an individual can be inspected in less than two seconds.

Materials readily capable of detection are those whose relative dielectric constant is larger than the barrier which they are behind, provided the barrier has losses low enough to permit the signal to penetrate and return. Materials whose relative dielectric constants are lower than the barrier materials may also be detected indirectly by shadowing due to other surrounding materials having higher relative dielectric constants. When high loss barriers (e.g., high relative dielectric constant [conductors]) are encountered, they can be detected and the contents behind or in them inspected manually.

Figure 6:
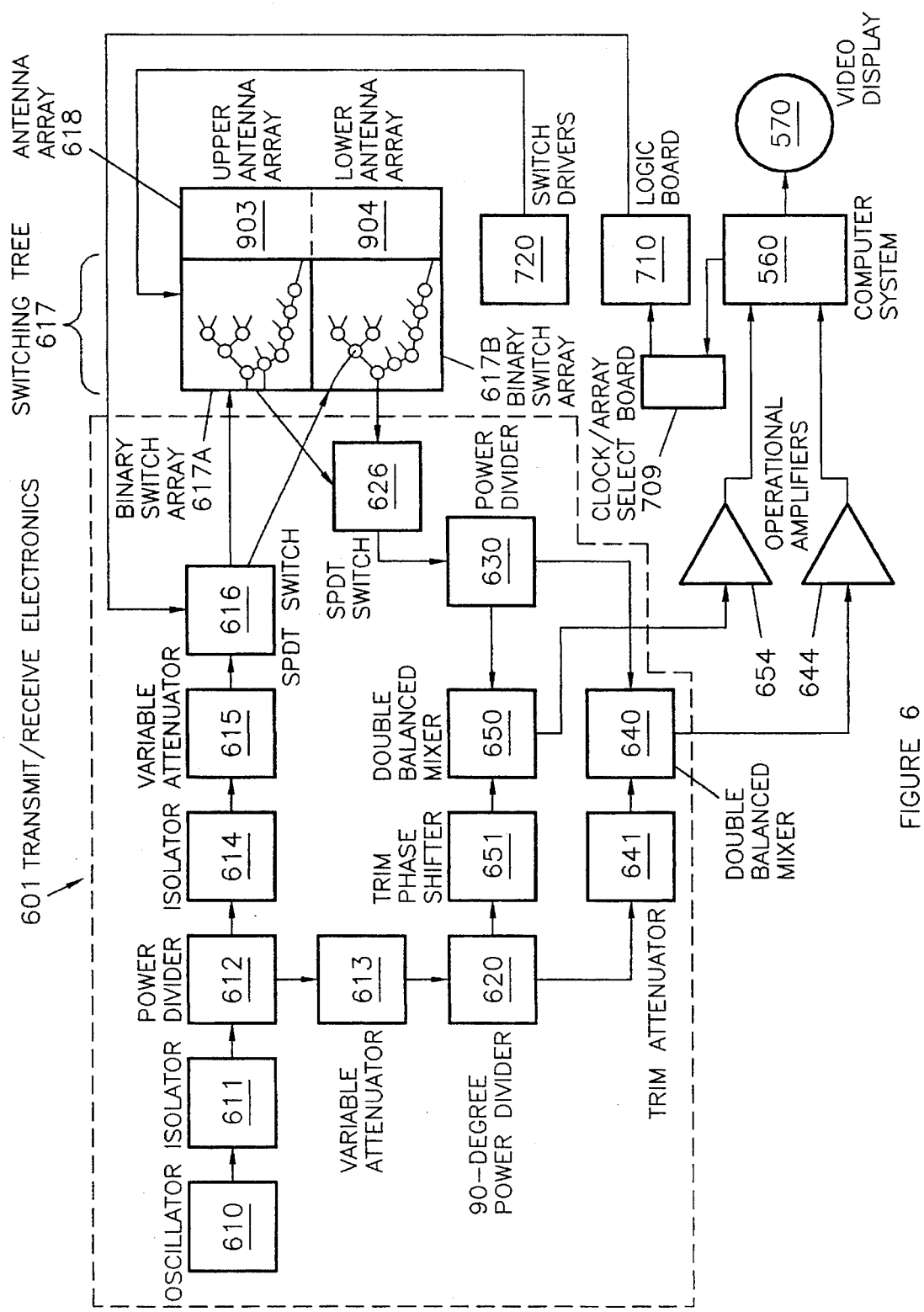
FIG. 6 shows a block diagram of a preferred embodiment of the invention.
Figure 7:
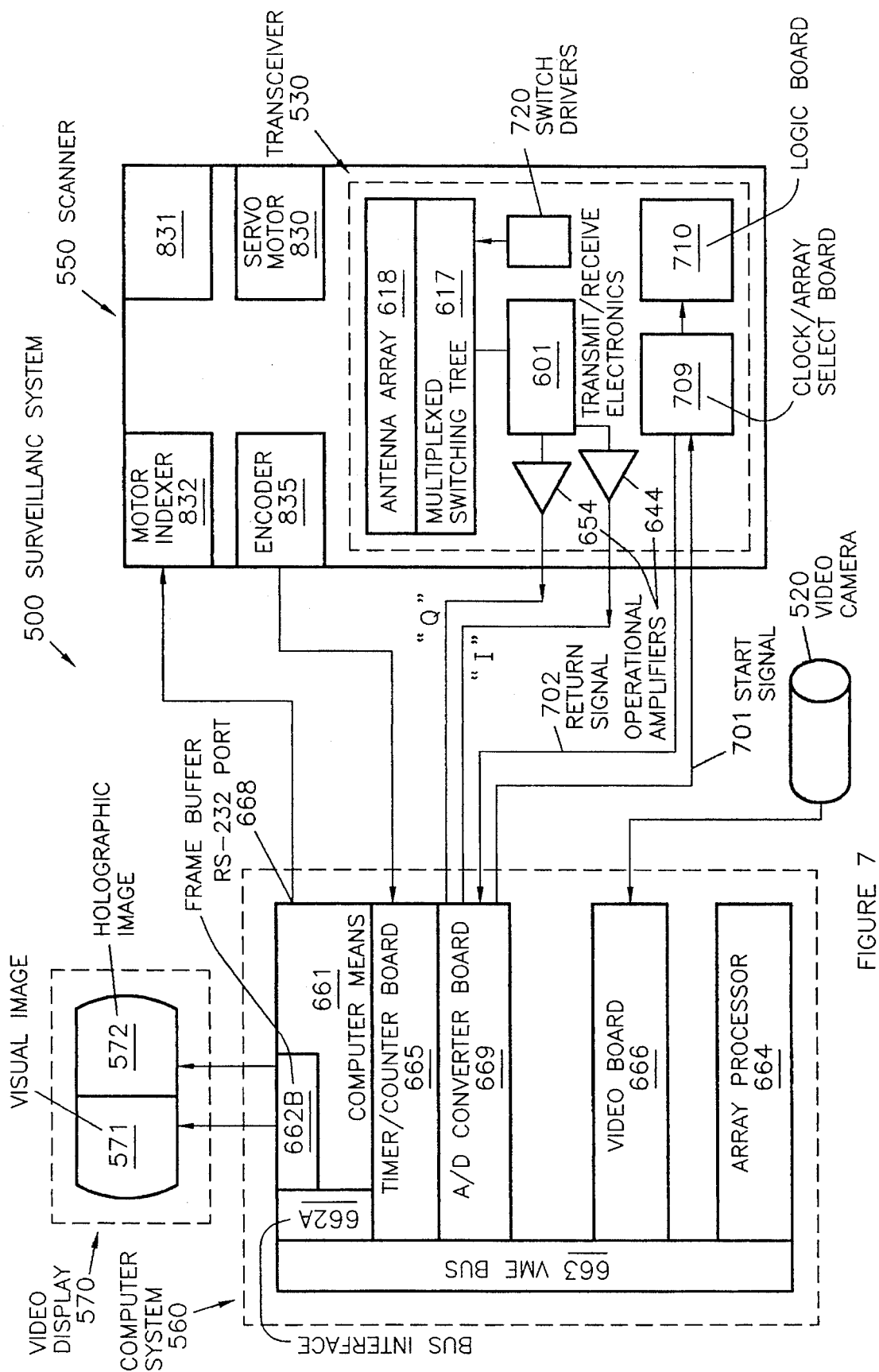
FIG. 7 shows the arrangement of interconnections of the computer and various control points in the overall system.
Figure 8:
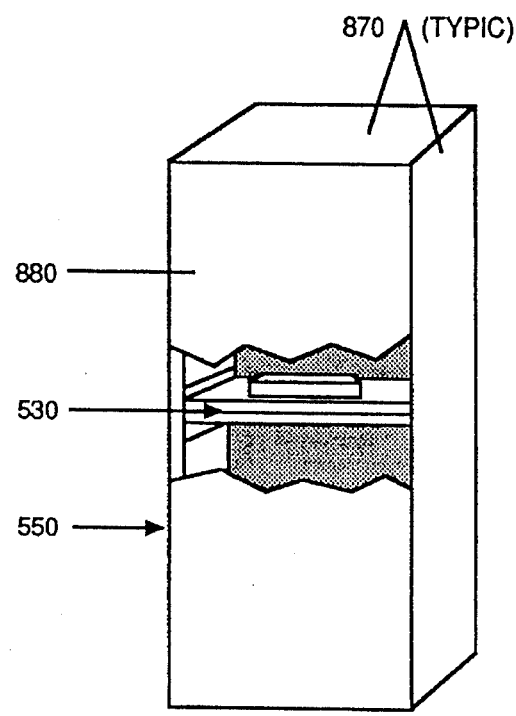
FIGS. 8A, 8B, and 8C depict an embodiment of a mechanical scanner useful in monitoring travelers at transportation centers such as airports.
Figure 8:
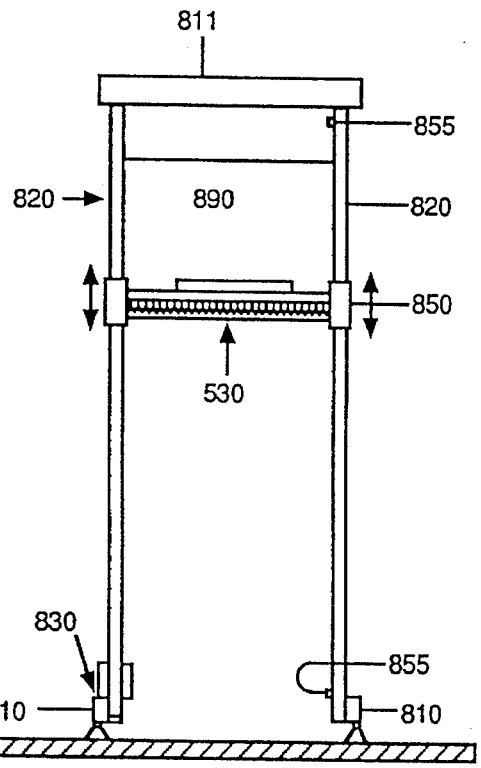
Figure 8:
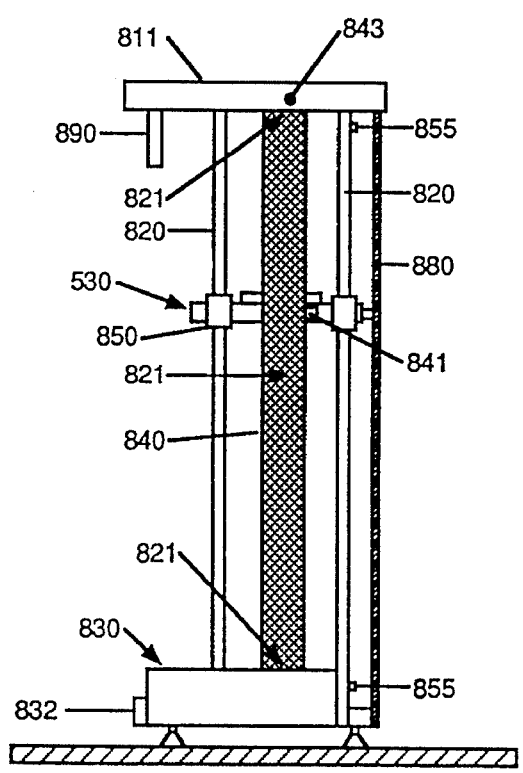

A presently preferred embodiment of the linear holographic surveillance system 500 is shown in FIGS. 6–12. Referring to FIGS. 6 and 7, there is shown the interconnection of the transmit/receive electronics 610 with switching means such as the multiplexed switching tree 617, the computer system 560, and logic board 710. The transceiver 530 is comprised of all but the computer system 560 and video display 570 of FIG. 6. The transceiver is a monostatic receiver that provides in-phase and quadrature amplitude and phase data in either continuous wave or pulse modes of operation. The transceiver 530 is preferably of waveguide component type construction and is interfaced with the multiplexed switching tree 617. The transmit/receive electronics 601 are shown within the dashed lines. Specifications for various critical components of the transceiver 530, scanner 550, and computer system 560 for a 35 GHz system are specified below.

The oscillator 610 provides the millimeter wave source energy signal for detecting the target and for reference signals. It is preferred that the oscillator 610 is a high Q cavity design with low noise spectrum output. The oscillator frequency is preferably from about 6 GHz to about 35 GHz±0.5 GHz with a temperature drift below about 0.160 MHz/°C. Output power should be sufficient to provide at least 50 mW at the antenna output. Signals from the oscillator 610 are sent to a first isolator 611 and are then divided by the first power divider 612 so that part of the signal is sent to a 90-degree power divider 620 through the first variable attenuator 613 for use as a reference signal in the double-balanced mixers 640,650 with the remainder of the signal transmitted to a second isolator 614. The 90-degree power divider 620 provides equal amplitude "local oscillator" drive signals to the double first and second double-balanced mixers 640,650 in quadrature (i.e., 90 degree phase difference). The amplitude and phase accuracy must be good enough to allow precise adjustment of amplitude balances with the trim attenuator 641 and phase in quadrature with the trim phase shifter 651. When mounted on a mechanical scanner, the trim attenuators should be lockable and not subject to change due to acceleration or deceleration forces. The isolators 611,614 are rectifying devices able to transmit millimeter waves in one direction (arrow), but not in the other, and should have an isolation of at least 20 dB. The first power divider 612 should have a coupling factor adequate to drive the double-balanced mixers 640,6S0 "local oscillator" port to a level that provides maximum dynamic range. The first variable attenuator 613 is used to select the ideal signal level to the double-balanced mixers 640,650. Output from the second isolator 614 is coupled to a second variable attenuator 615 which is preferably calibrated and has an attenuation range of at least 50 dB.

The output of the second variable attenuator 615 is coupled to a multiplexed switching tree 617 by a first single-pole, double-throw, SPDT-switch 616, which is controlled by the logic board 710. The switches in the multiplexed switching tree 617 are electronic millimeter wave switches, including but not limited to pin diode switches, ferrite switches, and field effect transistors. The switches in the multiplexed switching tree 617 are arranged and controlled so that the source power from the transceiver 530 can be routed to any waveguide and its associated antenna in a sequential fashion. The switches are driven by TTL-compatible switch drivers 720. The switch drivers 720 are addressable in a binary fashion so that they may be driven from a binary counter through a logic board 710, where the counter output corresponds to the selected antenna. The 128 leads from the output of the binary switch array 617A are interfaced to waveguides 901 on the antenna array 618.

Millimeter waves from the transceiver 530 are radiated by the antenna array 618. The antenna array 618 transmits the millimeter waves to the target, and also receives the target's reflected waves. The phase and amplitude data from the received waves is processed and sent to the computer system 560. Thus, the target is illuminated by a source of radiation from the antenna array 618. In the simple system shown in FIG. 1, the target was mechanically scanned horizontally and vertically by physically moving the antenna to the different positions in the x and y axis. In the presently preferred multi-unit (antenna) linear array system, the antenna array 618 on the transceiver 530 is electronically scanned in the horizontal direction and mechanically scanned in the vertical direction.

Referring again to FIG. 6, the switching means is preferably a set of two SPDT-switches 616,626 and a dual, multiplexed switching tree 617, such as a dual set of binary switching trees, which is comprised of switches 617C in a first and second binary switch array 617A,617B that directs outgoing millimeter wave signals to the appropriate antenna 1001 of the 128-element antenna array 618. Six layers of switches 617C are needed in each of the binary switch arrays 617A, 617B to obtain the required sixty-four outgoing/incoming channels in the upper antenna array 903, and sixty-four channels in the lower antenna array 904 of the antenna array 618. In FIG. 6, only some of the required switches 617C in the binary switch arrays 617A,617B are shown. Switches 617C in the binary switch arrays 617A, 617B are preferably pin diode switches when using first and second SPDT-switches 616,626. While a binary switching means has been described above, other switching means such as, for example, a comb-type transmission-line-sequential switching array with appropriate wiring and control adjustments can also be used.

Figure 9:
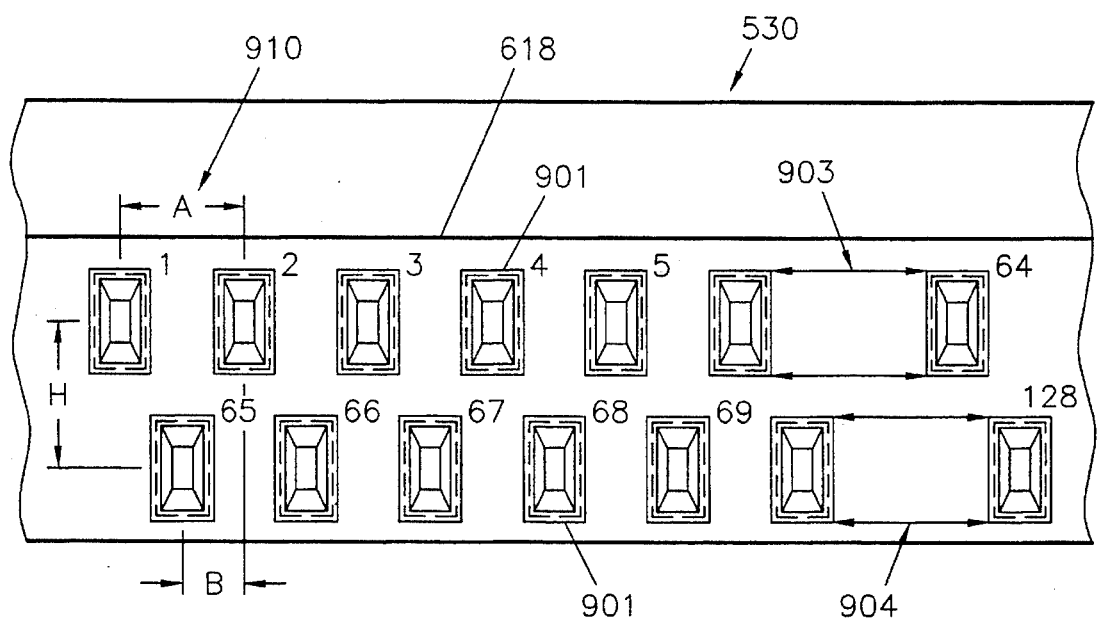
FIG. 9 shows the arrangement of the waveguides on the front of the antenna array.

With further reference to FIG. 6 and also to FIG. 9, the multiplexed switching tree 617 is controlled by the computer system 560 with commands through the logic board 710 that controls the switch drivers 720, and first and second binary switch arrays 617A,617B, respectively. The computer system 560 initiates the sequence with a signal at the start signal 701, which begins sequencing the signals by the clock/array select board 709. Both SPDT-switches 616,626 are single-pole, double-throw switches, controlled from the logic board 710. Both SPDT-switches 616,626 are appropriately timed so that when the first SPDT-switch 616 is "on" for the first binary switch array 617A (and "off" for the second binary switch array 617B), then the second SPDT-switch 626 is "on" for the second binary switch array 617B (and "off" for the first binary switch array 617A). Thus, when either SPDT-switch 616,626 is "on" for outgoing signals to the upper antenna array 903, the other SPDT-switch will be "on" to incoming signals from the lower antenna array 904, and vice versa. The reflected return signal is detected by the antenna array 618 and is sent to the second binary switch array 617B and appropriately switched to the second power divider 630, but not toward the second variable attenuator 615 by the first and second SPDT-switches 616,626. Interference between the incoming signals and outgoing signals is prevented, and improved separation attained by transmitting on one channel and simultaneously receiving on another channel. The preferred sequence is to sequentially transmit across the upper sixty-four channels (numbers 1–64 in FIG. 9) of the upper antenna array 903, while simultaneously sequentially receiving return signals with the lower sixty-four channels (numbers 65–128 in FIG. 9). Thus, when transmitting through upper antenna channel 1 with the first binary switch array 716A, signals are simultaneously received through the lower channel 65 with the second binary switch array 617B. When transmitting with upper channel 2, reception is through the lower channel 66, and so on. On the other hand, when transmitting through the lower antenna channel 65, reception is through upper channel 1; and when transmitting through the lower channel 66, reception is through upper channel 2, and so on.

Referring again to FIG. 6, the second power divider 630 is the input for the first and second balanced mixers. When the incoming signal reaches the second power divider 630, it is equally split into two channels to drive the "radio frequency" ports of the double-balanced mixers 640,650. The path length between the second power divider 630 and each of the double-balanced mixers 640,650 should be about equal to keep phase differences to a minimum. One channel is called the in-phase leg 640+ and the other is the quadrature leg 650+. Thus, the signal enters the double-balanced mixers 640,650, which detect the phase and amplitude of the signal. The double-balanced mixers 640,650 should be a matched pair selected for minimum conversion loss (less than 4.5 dB) and maximum dynamic range. The first double-balanced mixer 640 is referenced in phase to the oscillator 610 by the 90-degree power divider 620 through the trim attenuator 641. The second double-balanced mixer 650 is referenced to the oscillator signal from the 90-degree power divider 620 in quadrature (90 degrees) through the trim phase shifter 651. For optimum operation, the local oscillator signal power must be the same at the double-balanced mixers 640,650. Signals from the double-balanced mixers 640,650 are then further processed similarly to the process described for FIG. 1 by the operational amplifiers 644,654, and converted to digital form in the A/D converter board 669 for further computation by the computer system 560 and viewing on the video display 570. Low frequency filters may not be needed before the operational amplifiers 644,654 (see FIG. 1) if there is enough inductance in the circuits to remove the 35 GHz signal prior to this point.

Refer now to FIG. 7, which shows details of the interconnection of the computer system 560 with the drive system of the scanner 550 and the transceiver 530. Computer means 661, such as a Computer System SUN 4/370 GX 661, is used for control and calculations for reconstruction of the holograms. This computer is a Reduced Instruction Set (RISC) computer with a bus interface 662A, a VME bus 663, and has 32 Mbytes of memory and a 670 Mbyte hard drive. An array processor 664, such as a Skybolt array processor, based on the Intel 860 & 960 chip set, having a maximum speed capability of about 80 MflopS, is used to accelerate the math operation discussed in the holographic algorithm above. A start signal 701 is sent to the clock/array select board 709 for initiating and controlling the sequence to the logic board 710. A return data valid signal 702 is used to confirm that data from the "I" and "Q" channels are ready to be received by the A/D converter board 669. The logic board 710 determines which channel is "on" in the antenna array 618. The encoder 835 provides the computer system 560 the vertical position where the holographic array assembly is on the scanner 550. The computer system 560 determines when a horizontal scan is necessary and sends the start signal 701 to initiate the scanning process. The antenna array 618 is sequentially scanned to the individual waveguides 901, first through the upper antenna array 903 and then through the lower antenna array 904. The data from each channel is sent back to the computer system 560 through the multiplexed switching tree 617 as discussed above. After scanning through the upper and lower antenna array 903,904 once, the scanning is stopped and the transceiver 530 waits for the next "start" command from the computer system 560 when it is in its next appropriate vertical position on the scanner 550. If desired, scanning can be initiated at the lower array rather than the upper array.

The A/D converter board 669 is preferably a high speed analog input board for the VME bus 663, with associated A/D software driver having a speed of at least 200 kHz and capacity of at least 8 bytes. It is used to capture the analog amplitude and phase information signals from the transceiver 530 and convert them to digital form. The timer/counter board 665 for the VME bus 663 is used to control the timing sequence for the transceiver 530 based on positional information provided by the encoder. The video board 666 provides a high resolution frame grabber and is used for displaying an optical picture obtained from the video camera 520 on an optional video display 570 that preferably provides a visual image 571 along with a 35 GHz holographic image 572 of an individual. The frame buffer 662B interfaces the computer with the video display 570 that may consist of a visual image 571, a holographic image 572, or other output means. The servomotor 830 on the scanner 550 is controlled by the motor driver 831 and motor indexer 832 that obtains control signals from the computer system 560 through the RS-232 port 668.

Referring now to FIGS. 8A, 8B, and 8C, in a presently preferred embodiment, scanner means such as the scanner 550 is capable of moving a transceiver 530 vertically at a distance and at a rate that allows appropriately rapid scanning of the target. The scanner 550 includes a support means such as a base 810 and upper frame 811; support beams 820; a motor drive system such as a servomotor 830 and associated controls (see FIG. 7); a belt drive system, such as belt 840, belt attachment 841, and support pulley 843; and guide 850 for slidable attachment to support beams 820. The scanner 550 is preferably constructed with panels 870 of metal or plastic to provide soundproofing and physical protection during scanner operation. The front of the scanner 550 is preferably covered with a window panel 880 fabricated from special low-loss millimeter wave window material such as Rexolite™. Other materials that can be used include low loss tangent materials such as those that are usable in radomes (e.g., Nylon, Lucite, and the like). In addition to having low loss, the materials should also be rigid. The window panel 880 should preferably not be so thick so as to substantially reduce sensitivity. At frequencies of about 110 GHz and below, it should be no more than about one wavelength thick. While FIGS. 8B–8C depict four beams 820 on which the transceiver 530 is slidably attached, it is presently preferred to use two beams with the beams between positions 821 at the center of the sides of the transceiver 530, see FIG. 8C. This reduces the chances of binding during the mechanical scan. Limit switches 855 provide control for stopping the array assembly.

The scanner 550 can be operated in three modes of operation:

1. Automatic Mode: When a scan command is sent from the computer system 560 to the logic board 710 and motor indexer 832, the transceiver 530 will scan a predetermined test aperture, stop, and wait for another command. When a second scan command is sent, the transceiver 530 will be scanned to the other end of the predetermined aperture and wait for another command. This routine can be repeated as long as scan commands are issued.

2. Calibration Mode: Calibration Procedure for Holographic Arrays.

As is apparent to those skilled in the art, a calibration procedure to correct for offsets and phase/amplitude variations in each holographic array channel is necessary for array normalization. This calibration process forces the holographic array to appear like a single element holographic system. Without this calibration processing, holographic imaging with array technology would not be possible. When a calibration command is sent to the motor indexer 832, the calibration procedure is performed in two steps. The first step is to correct for offsets, which step is performed by electronically scanning each antenna 1001 channel without a high reflective object in front of the transceiver 530, and store the offset values in the computer system 560. The stored offset values are used to force the array element offsets to the same value by appropriate calculations. The second calibration procedure is performed with a flat metal plate 890 that is perpendicular to the antenna array 618 on the transceiver 530, see FIG. 8B–8C. Each of the 128 channels has a different phase and amplitude associated with it before calibration. The flat metal plate 890 provides a standard reference in which the phase and amplitude of each channel can be calibrated. This second calibration can be performed in the computer in a similar fashion as the first.

3. Manual Mode: The transceiver 530 can be positioned anywhere in the aperture using a manual controller. The manual controller may be part of the motor indexer 832.

The drive system is controlled by the motor indexer 832 that is interfaced to the computer by a standard interface such as an RS-232. An example is stepper or servomotors controlled by a Parker Computer C3000 indexer. Scan speed should be appropriate to the target to be examined but can vary from about one to several seconds for a mechanical scanner to milliseconds for a totally electronic scanner for a seven-foot scan aperture. An aperture scan for evaluation of human subjects at a transport facility, for example, must be fast enough so that movement of the individual does not interfere with the scanned image. While this can be accomplished with a fully electronic scanner, in the case of a mechanical scanner, depending on the speed of the scan, moving objects or living subjects will ordinarily need to remain still for the duration of the scan. It is understood that in the preferred embodiment, as the transceiver 530 is electrically scanned across its width, it is simultaneously scanned mechanically in a vertical direction. To provide good images it is preferred that one horizontal scan of both the upper and lower antenna arrays be complete before the antenna array assembly has moved one-tenth wavelength vertically; otherwise, the phase differences across the array may cause image degradation.

The antenna unit array 68 uses waveguide (WR-28) for the KA-band, 26.5–40 GHz, arranged so the waveguide ends form two 64-antenna rows at the antenna end with the orientation and spacing shown in FIG. 9. Waveguide up to and including the W-band can be used. An antenna unit is the minimum necessary to both send and receive millimeter wave radiation. In a preferred monostatic system as shown, an individual antenna is an antenna unit. In a bistatic system, two individual antennae form an antenna unit with a first individual antenna sending millimeter wave radiation, and a second individual antenna receiving the reflection signal. In a bistatic system there is greater sensitivity because of greater isolation between transmitter and receiver compared to a monostatic system, thereby permitting the target to be further from the antenna and still obtain a high resolution image. The antennae used are low-gain, end-fired antennae. Low-gain, end-fired antennae include but are not limited to polyrod antenna, printed circuit antennae, and other tapered slot antennae.

Figure 10A:
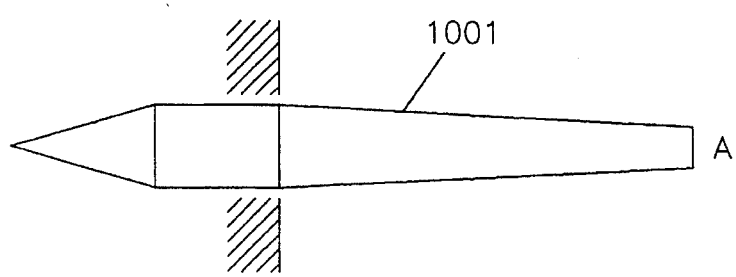
FIG. 10 shows a side view, A, and top view, B, of a typical antenna useful at 35 GHz.
Figure 10B:
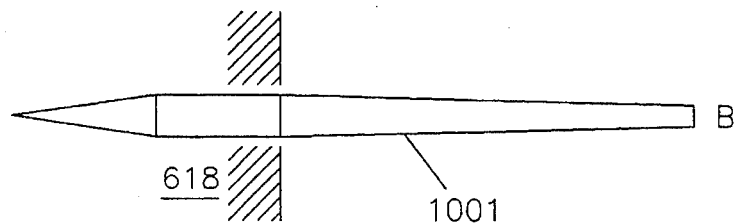
Figure 11:
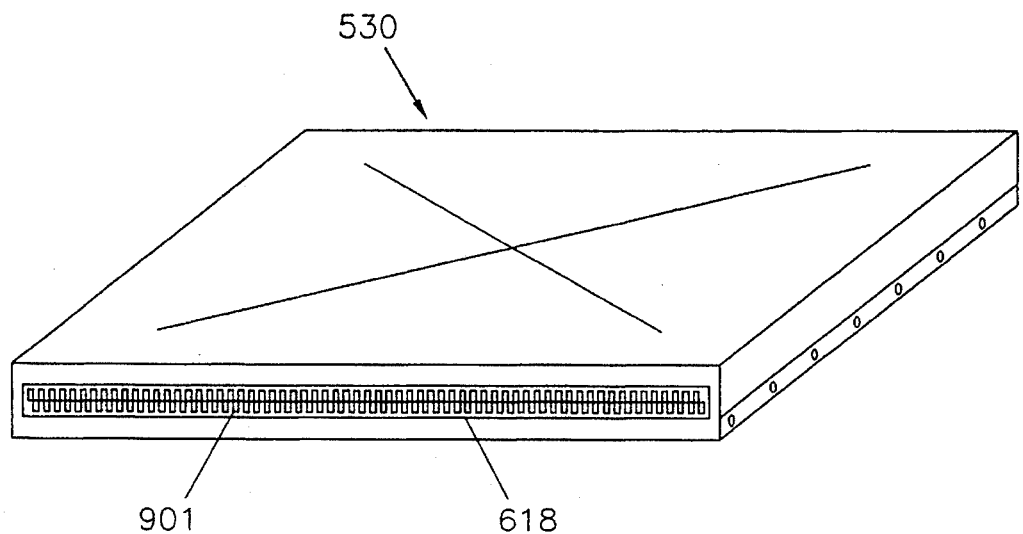
FIG. 11 shows the arrangement of the 128 antenna on the antenna array 618.

FIG. 9 shows the arrangement of the upper and lower antenna array 903,904 on the front of the antenna array 618. Waveguide spacing dimensions are given for 35 GHz. These dimensions can be varied within the limits of frequency and desired resolution of the obtained image. To obtain the best possible resolution of the final image, the waveguides need to be as close together as possible. In addition to using closer antenna spacing, resolution of the image can also be increased by operating at higher frequencies. Higher frequencies than the W-band are contemplated in the invention and would of course provide even greater resolution. For example, to obtain the tightest possible grouping at 35 GHz, without physical interference of the waveguides, the vertical spacing H is about 1½ wavelengths, while the horizontal spacing A is about 1⅓ wavelengths. The upper antenna array 903 and lower antenna array 904 are offset by distance B which is preferably ½A. The polygonal antenna 1001 fit into the waveguides 901. Individual channel numbers (1–128) are noted next to the upper and lower waveguides 901. FIG. 10 shows a side view, A, and top view, B, of a typical antenna 1001 useful at 35 GHz, while FIG. 11 shows the general arrangement of the antenna array 618 on the front of the transceiver 530.

The maximum number of antenna elements is determined by the frequency of the array and the array width, or area to be covered. The higher the frequency the more elements may be incorporated since the major limitation on increasing the number of elements is basically the size of the waveguide. In FIGS. 9 and 10 this limitation is readily apparent by the waveguide spacing. Here it is seen that the individual antenna are sized to fit directly in the waveguide and thus the waveguide size is 5 the limitation on the array. The higher the number of elements for a given area, the greater will be the resolving power of the device. This is of course limited by the wavelength of the millimeter waves used. In order to obtain higher frequency operation, waveguide and/or antenna fabricated by techniques such as those for microstrip patch antenna that allows closer spacings are contemplated. For example, as a rule of thumb, the resolving power of a detection system is about one wavelength, although theoretically one would expect it to be one-half the wavelength. Thus, at 26.5 GHz the resolution is limited to about 1.13 cm (theoretical is 0.57 cm), while at 110 GHz the resolution is limited to about 0.27 cm (theoretical is 0.14 cm).

The beam width of the polyrod antenna 1001 determines the lateral resolution (f#) of the linear holographic surveillance system 500. To increase lateral resolution, the beam width of the polyrod antenna 1001 must be increased. It is preferred that the beam width and distance to the target result in low f-numbers, preferably between about 0.1 to about 10, and most preferably from about 1 to about 3. It is preferred that the beam width of the antenna range from about 10 degrees to about 50 degrees, and it is most preferred that the beam width be about 30 degrees.

By increasing the antenna beam width, the gain of the antenna is decreased; however, this decreases sensitivity to reflected target signals. In addition, increasing the antenna beam width can create mutual coupling problems between antennas in linear and two dimensional holographic arrays. Mutual coupling problems can degrade the image quality. Typically, the polyrod antenna beam width is chosen so that the highest spatial frequency that can be captured in a holographic detection system is one wavelength. To meet the Nyquist sampling criteria, the aperture must be sampled at least every one-half wavelength. In the preferred method discussed above, the sampling in the horizontal dimension is fixed by the array spacing between elements. (See FIG. 9, where space A 910 between channels 1 and 2 is the array spacing). This spacing in the present system is twothirds of a wavelength and therefore does not meet the Nyquist sampling criteria. However, this spacing was chosen as a compromise between the antenna gain and beam width, possible aliasing in the imaging due to under sampling of a high spatial frequency target, and mutual coupling problems between antennas. The spacing 910 may be varied between about ½ to about ¾ wavelength with the optimum dimension being easily chosen for a particular frequency, and application by those skilled in the art.

As will be appreciated by those skilled in the art, the antenna array could also be arranged so as to be mechanically scanned horizontally, circularly, or to be arranged as a two-dimensional array and have sufficient antenna placed so as not to require mechanical scanning. If desired, two or more antenna arrays 550 could be arranged so as to scan any of the four vertical or two horizontal geometric planes of a subject; i.e., sides, top, and/or bottom. FIG. 5 shows an additional transceiver and scanner 555 to accomplish this. One or more additional scanners 555 are useful since the millimeter waves do not penetrate the human body like x-rays, and therefore only one surface of the body is revealed during a scan.

Figure 12:
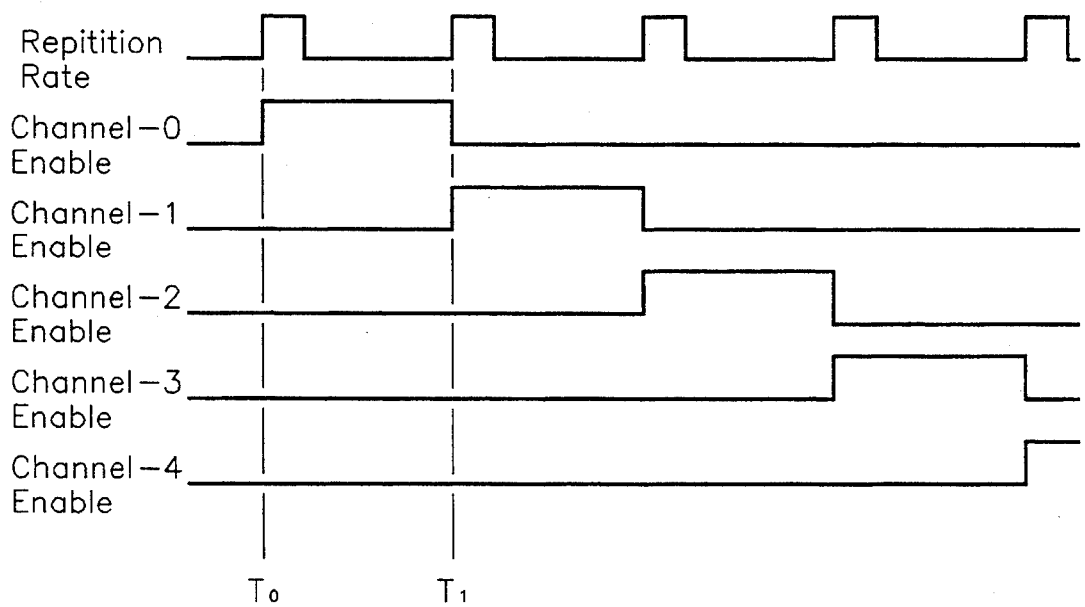
FIG. 12 shows the timing sequence for the individual channels of the multiplexed switching tree.

FIG. 12 shows the general timing sequence for an outgoing signal for the first four individual channels of the antenna array 618. Each channel should ordinarily be "on" about 1 to 1.5 μsec at a frequency of 35 GHz at the repetition rate provided by the clock. The remaining 124 channels are sequenced similarly, with channels 5 to 64 addressed first, then channels 65 to 128.

Initially, systems operating at frequencies of 35 GHz and 90 GHz were demonstrated. However, systems have been found operable with frequencies ranging from about 1 GHz to about 110 GHz and above. Preferred systems operate from about 6 GHz to about 35 GHz, because frequency generators are less expensive in that range.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit or scope of the invention.

REFERENCES

Although the below-listed references discuss acoustical holography, the same principles as disclosed therein are applicable to the understanding of the present invention.

1. Boyer, et al. 1970. "Reconstruction of Ultrasonics Image by Backward Propagation," in *Acoustical Holography*, Vol. 3, pp. 333–384, Ed. A. Metherall, Plenum Press, New York.
2. Gabor, D. 1948. "A New Microscopy Principle, " *Nature* Vol 161, pp. 171–178.
3. Gabor, D. 1949. "Microscopy by Reconstructed Wavefronts," *Proceedings of the Royal Society*, Vol. A197; pp. 454–456.
4. Gabor, D. 1951. "Microscopy by Reconstructed Wavefronts," *Proceedings of the Physical Society*, Vol. B64; pp. 499–500.
5. Goodman, J. W. 1968. *Introduction to Fourier Optics*, pp. 129–131, McGraw Hill, New York.
6. Hildebrand, B. P. and K. Haines. 1969. "Holography by Scanning," *Journal of the Optical Society of America*, Vol. 59; pp. 1–6.
7. Hildebrand, B. P., et al. 1979. "An Experiment in Seismic Imaging," *Acoustical Imaging and Holography*, Vol. 1, No. 2. Crane, Russok & Company, Inc., New York.

We claim:

1. A holographic apparatus for near real-time imaging of a target, said apparatus utilizing millimeter wave radiation having a frequency from about 1 to about 110 GHz, comprising:
   (a) a holographic array having a plurality of low-gain, end-fire antenna units spaced apart from about 0.25 to about 1.5 wavelength, wherein each unit both sends and receives millimeter wave radiation, said units connected by a plurality of electronic millimeter wave switches permitting sequential operation of said units, said array spaced apart from said target with a low f-number;
   (b) a holographic transceiver system means for operating said units and providing each unit with millimeter wave radiation source, then receiving high frequency millimeter wave radiation reflection from said target and collected by the unit, then making an analog oscillated reference signal, together with an analog reflected target signal;
   (c) a real-to-imaginary converter for converting the analog oscillated reference signal and the analog reflected target signal to an analog real part of a hologram and an analog imaginary part of the hologram;
   (d) an analog to digital converter for converting said analog real part and said analog imaginary part to corresponding digital parts; and
   (e) a computer for applying a backward wave propagation algorithm that preserves the low f-number to the digital real and digital imaginary parts of the hologram to reconstruct a holographic image.

2. The apparatus as recited in claim 1, wherein said antenna elements have a beam width from about 10 degrees to about 50 degrees.

3. The apparatus as recited in claim 1, wherein said low-gain, end-fire antenna units are monostatic.

4. The apparatus as recited in claim 1, wherein said low-gain, end-fire antenna units are bistatic.

5. The apparatus as recited in claim 2, wherein the low-gain, end-fire antenna units are polyrod antennas.

6. The apparatus as recited in claim 2, wherein the low-gain, end-fire antenna units are printed circuit antennas.

7. The apparatus as recited in claim 1, wherein the electronic millimeter wave switch is a first set of pin diode switches in a first and second binary switch array, and a second set of ferrite switches that directs outgoing millimeter wave signals to the successive antenna unit.

8. The apparatus as recited in claim 1, wherein the low f-number is from about 1 to about 3.

9. The holographic apparatus as recited in claim 1, wherein the computer for applying the backward wave propagation algorithm comprises:
   (a) a digital computer having,
      (i) a first set of instructions for computing a two-dimensional Fourier transform of a given field f(x, y,z) from phase and amplitude information obtained from the oscillated reference digital signal and from the reflected target digital signal,
      (ii) a second set of instructions for multiplying the two-dimensional Fourier transform by a complex backward wave propagator and forming a backward wave product, (iii) a third set of instructions for computing an inverse transform of a plane wave angular spectrum at the target plane yielding a target image, and (iv) a fourth set of instructions for computing a target intensity image from the target image.

10. The holographic apparatus as recited in claim 1, said array comprises:

a linear array, moved by a mechanical means during transmission and receipt of said high frequency millimeter wave radiation, thereby providing a simultaneous scan of source and reflection millimeter wave radiation.

11. The holographic apparatus as recited in claim 10, wherein the linear array comprises:

(a) an upper horizontal row, and (b) a lower horizontal row wherein the two rows are offset by half the spacing between antenna elements, thereby enhancing vertical resolution as the upper and lower horizontal rows are moved vertically.

12. The holographic apparatus as recited in claim 10, wherein the two arrays are moved across an aperture in less than two seconds.

13. The holographic apparatus as recited in claim 1, wherein a plurality of antenna elements are spaced in a stationary, multi-dimensional array.

14. The apparatus as recited in claim 13, wherein a multi-dimensional array is a planar two-dimensional array that is electronically scanned in less than 0.5 seconds.

15. A method of holographic surveillance, comprising the steps of:

(a) scanning an aperture with a holographic array having a plurality of low-gain, end-fire antenna units spaced apart from about 0.25 to about 1.5 wavelength, wherein each unit both sends and receives millimeter wave radiation, said units connected by a plurality of electronic millimeter wave switch means permitting sequential operation of said units, said array spaced apart from said target with a low f-number;

(b) operating individual antenna elements with a holographic transceiver system means for operating said units and providing each unit with millimeter wave radiation source, then receiving high frequency millimeter wave radiation reflection from said target and collected by the unit, then making an analog oscillated reference signal together with an analog reflected target signal;

(c) converting the analog oscillated reference signal and the analog reflected target signal to an analog real part of a hologram and an analog imaginary part of the hologram;

(d) converting said analog real part and said analog imaginary part to corresponding digital parts; and (e) applying a backward wave propagation algorithm that preserves the low f-number to the digital real and digital imaginary parts of the hologram to reconstruct a holographic image.

16. The method of holographic surveillance as recited in claim 15, wherein applying the backward wave propagation algorithm comprises:

(a) computing a two-dimensional Fourier transform of a given field $f(x,y,z)$ from phase and amplitude information obtained from the oscillated reference digital signal and from the reflected target digital signal;

(b) multiplying the two-dimensional Fourier transform by a complex backward wave propagator and forming a backward wave product;

(c) computing an inverse transform of the backward wave product yielding target image; and (d) computing a target intensity image from the target image.

17. The method of holographic surveillance as recited in claim 15, wherein the low f-number is from about 1 to about 3.

18. An apparatus for near real-time holographic imaging of a target, comprising:

(a) a holographic array having a plurality of low-gain, end-fire antenna units spaced apart from about 0.25 to about 1.5 wavelength, wherein each unit both sends and receives millimeter wave radiation having a frequency from about 26.5 to about 110 GHz, said units connected by a plurality of electronic millimeter wave switches permitting sequential operation of said units, said holographic array spaced apart from said target with a low f-number of from about 0.1 to about 10;

(b) a holographic transceiver that provides millimeter wave energy to the units, then receives millimeter wave reflection from said target and collected by the units, and converts the reflected millimeter wave energy together with an oscillator to an analog real part of a hologram and an analog imaginary part of a hologram;

(c) an analog to digital converter that converts the analog real part and the analog imaginary parts of the hologram to corresponding digital parts; and (d) a backward wave propagator that reconstructs a holographic image from the real and imaginary digital parts and preserves the low f-number.

* * * * *

UNITED STATES PATENT AND TRADEMARK OFFICE
CERTIFICATE OF CORRECTION

PATENT NO. : 5,455,590
DATED : October 3, 1995
INVENTOR(S) : Collins et al.

It is certified that error appears in the above-indentified patent and that said Letters Patent is hereby corrected as shown below:

Column 10, line 9    Replace the number "34" with --340--.

Column 11, line 39   Replace "6S0" with the number --650--.

Column 15, line 47   Replace "68" with the number --618--.

Signed and Sealed this

Twenty-eighth Day of October, 1997

Attest:

BRUCE LEHMAN

Attesting Officer

Commissioner of Patents and Trademarks